US012783606B2

(12) United States Patent
Hsieh et al.

(10) Patent No.: US 12,783,606 B2
(45) Date of Patent: Nov. 3, 2026

(54) DATA SPLITTING SYSTEM AND METHOD FOR VALIDATING MACHINE LEARNING

(71) Applicants: Inventec (Pudong) Technology Corporation, Shanghai (CN); INVENTEC CORPORATION, Taipei (TW)

(72) Inventors: Wan-Ting Hsieh, Taipei (TW); Sergio Gonzalez-vazquez, Taipei (TW); Trista Pei-Chun Chen, Taipei (TW)

(73) Assignee: Inventec (Pudong) Technology Corporation, Shanghai (CN)

( * ) Notice: Subject to any disclaimer, the term of this patent is extended or adjusted under 35 U.S.C. 154(b) by 1013 days.

(21) Appl. No.: 17/847,308

(22) Filed: Jun. 23, 2022

(65) Prior Publication Data

US 2023/0385380 A1 Nov. 30, 2023

(30) Foreign Application Priority Data

Jun. 6, 2022 (CN) ......................... 202210628846.4

(51) Int. Cl.

*G06F 18/21* (2023.01)
*A61B 5/021* (2006.01)
*G06F 18/2115* (2023.01)

(52) U.S. Cl.

CPC .......... *G06F 18/2193* (2023.01); *A61B 5/021* (2013.01); *G06F 18/2115* (2023.01)

(58) Field of Classification Search

None
See application file for complete search history.

(56) References Cited

U.S. PATENT DOCUMENTS 9,511,120 B2 * 12/2016 Ocaranza Jeraldino ..................... A61K 38/4813
10,716,518 B2 * 7/2020 Basu ......................... A61B 5/33
10,980,429 B2 * 4/2021 Paul ...................... A61B 5/7264
11,083,385 B2 * 8/2021 Leem ..................... A61B 5/021
2004/0030261 A1 * 2/2004 Rantala ................ A61B 5/0285 600/561
2004/0167417 A1 * 8/2004 Schulhauser ........ A61B 5/0006 600/513
2005/0119578 A1 * 6/2005 Kubo ................... A61B 5/0225 600/490

(Continued)

*Primary Examiner* — Maikhanh Nguyen

(74) *Attorney, Agent, or Firm* — Troutman Pepper Locke LLP; Tim Tingkang Xia, Esq.

(57) ABSTRACT

A data splitting method for validating machine learning is adapted to a BP (blood pressure) dataset having a plurality of subjects and includes: dividing measurement ranges of the SBP (systolic blood pressure) data and the DBP (diastolic blood pressure) data into first intervals and second intervals; generating a plurality of classes according to the first and second intervals, wherein each class includes one of the first intervals and one of the second intervals; determining and recording a match condition of the BP data of each subject and classes, and thereby generating a plurality of match conditions corresponding the plurality of subjects, wherein each match condition includes a plurality of labels corresponding to the classes, each label has a first state or a second state; and performing a distribution procedure according to the matching conditions to distribute the BP data of subjects into a plurality of subsets.

8 Claims, 6 Drawing Sheets

(56) References Cited

U.S. PATENT DOCUMENTS

| | | | | | |
|---|---|---|---|---|---|
| 2005/0251059 | A1* | 11/2005 | Kim | A61B 5/681 | 600/513 |
| 2005/0261593 | A1* | 11/2005 | Zhang | A61B 5/02125 | 600/513 |
| 2009/0062667 | A1* | 3/2009 | Fayram | A61B 5/349 | 607/23 |
| 2012/0071768 | A1* | 3/2012 | Yamakoshi | A61B 5/6824 | 600/499 |
| 2013/0226010 | A1* | 8/2013 | Hotta | A61B 5/025 | 600/490 |
| 2013/0237776 | A1* | 9/2013 | Ong | A61B 5/7275 | 600/301 |
| 2014/0031646 | A1* | 1/2014 | Yakirevich | A61B 5/7239 | 600/310 |
| 2015/0327785 | A1* | 11/2015 | Lading | A61B 5/726 | 600/480 |
| 2016/0270668 | A1* | 9/2016 | Gil | A61B 5/14551 | |

* cited by examiner

DATA SPLITTING SYSTEM AND METHOD FOR VALIDATING MACHINE LEARNING

CROSS-REFERENCE TO RELATED APPLICATIONS

This non-provisional application claims priority under 35 U.S.C. § 119(a) on Patent Application No(s). 202210608019.9 filed in China on May 31, 2022, the entire contents of which are hereby incorporated by reference.

BACKGROUND

1. Technical Field

The present disclosure relates to machine learning, and more particular to a data splitting system and method for validating machine learning.

2. Related Art

Validation strategies are essential for training and tuning the hyper-parameters of Machine Learning (ML) and Deep Learning (DL) models. With data splitting (or cross-validation) techniques, data is partitioned into training, validation and test sets for training and validation purposes. This provides insight regarding the accuracy and generalization of the models on independent and unseen sets. And consequently, they allow recognition of problems such as overfitting or bias, and to select the best models accordingly.

Many Cross-Validation (CV) variants, such as Leave-One-Out, Holdout and K-fold CV, are common practices in standard ML problems, like regression problems. However, Blood Pressure (BP) estimation is not a standard regression problem. For instance, the data points of the BP datasets are not completely independent of each other. That is, these datasets often have many segments coming from the same record or subject, which may contain very similar information. In addition, there are two targets in a BP estimation problem, Systolic BP (SBP) and Diastolic BP (DBP), which are more akin to a multi-task or multi-output regression problem. Finally, the distribution of SBP and DBP are often skewed, since extreme BPs are much rarer, it becomes an imbalance regression problem.

These differences must be considered in order to correctly partition the data during the cross-validation. For example, randomly partitioning the data could lead to segments of the same subject being in the training, validation and test sets at the same time. Since the segments from the same subject could carry similar information, this would result in the breakdown of independence between sets and bring the over-optimistic results. Moreover, due to the skewed and imbalance distribution, a random data partitioning could cause problems such as different distributions between each partition or data shift, and even the rare cases missing in the test set.

SUMMARY

Accordingly, the present disclosure provides a data splitting system and method for validating machine learning to prevent from the above problems. The cross-validation of BP estimation task can keep the data of the same subject in the same set, and maintain the distribution of SBP and DBP in different datasets as much as possible. In other words, when the datasets are generated by applying the present disclosure, the BP data, no matter the data is SBP or DBP, there is a high similarity between multiple trends presented in multiple datasets.

According to an embodiment of the present disclosure, a data splitting method for validating machine learning adapted to a BP (blood pressure) dataset, wherein the BP dataset comprises a plurality of subjects, each of the plurality of subjects comprises a plurality of BP data, and the plurality of BP data of each subject includes a plurality of SBP (systolic blood pressure) data and a plurality of DBP (diastolic blood pressure) data, and the method comprises following steps performed by a computing device: dividing a measurement range of the SBP data into a plurality of first intervals and dividing a measurement range of the DBP data into a plurality of second intervals; generating a plurality of classes according to the plurality of first intervals and the plurality of second intervals, wherein each of the plurality of classes comprises one of the plurality of first intervals and one of the plurality of second intervals; determining and recording a match condition of the plurality of blood pressure data of each of the plurality of subjects and the plurality of classes, and thereby generating a plurality of match conditions corresponding the plurality of subjects, wherein each of the plurality of match conditions comprises a plurality of labels corresponding to the plurality of classes, each of the plurality of labels has one of a first state and a second state, the first state represents that one of the plurality of SBP data belongs to the first interval corresponding to the label corresponding to the class and one of the plurality of DBP data belongs to the second interval corresponding to the label corresponding to the class, and the second state represents that the plurality of BP data do not match the class corresponding to the label; and performing a distribution procedure according to the plurality of matching conditions to distribute the plurality of BP data of the plurality of subjects into a plurality of subsets.

According to an embodiment of the present disclosure, a data splitting system for validating machine learning comprising: a measurement device configured to generate a BP (blood pressure) dataset, wherein the BP dataset comprises a plurality of subjects, each of the plurality of subjects comprises a plurality of BP data and the plurality of BP data of each subject includes a plurality of SBP (systolic blood pressure) data and a plurality of DBP (diastolic blood pressure) data; a storage device communicably connecting to the measurement device for receiving and storing the BP dataset, and configured to store a computer-readable recording medium; and a computing device communicably connecting to the storage device, wherein the computing device is configured to execute the computer-readable recording medium to perform following steps: dividing a measurement range of the SBP data into a plurality of first intervals and dividing a measurement range of the DBP data into a plurality of second intervals; generating a plurality of classes according to the plurality of first intervals and the plurality of second intervals, wherein each of the plurality of classes comprises one of the plurality of first intervals and one of the plurality of second intervals; determining and recording a match condition of the plurality of blood pressure data of each of the plurality of subjects and the plurality of classes, and thereby generating a plurality of match conditions corresponding the plurality of subjects, wherein each of the plurality of match conditions comprises a plurality of labels corresponding to the plurality of classes, each of the plurality of labels has one of a first state and a second state, the first state represents that one of the plurality of SBP data belongs to the first interval corresponding to the label corresponding to the class and one of the plurality of DBP data belongs to the second interval corresponding to the label corresponding to the class, and the second state represents that the plurality of BP data do not match the class corresponding to the label; and performing a distribution procedure according to the plurality of matching conditions to distribute the plurality of BP data of the plurality of subjects into a plurality of subsets.

In view of the above, the data splitting system and method for validating machine learning proposed in the present disclosure have the following contributions or effects: (1) The proposed method keeps all samples from the same subject in the same set (either training set or test set); (2) The proposed method is able to achieve similar BP distribution in training, validation and test sets; and. (3) The proposed method is able to maintain the BP distribution of different sets when there are multiple constraints, meaning SBP distribution of training/validation and test sets are similar and at the same time, DBP distribution of different sets could also be similar. Said multiple constraints include SBP and DBP, and may further include any constraints related to BP, such as pulse rate, heartbeat, that affect model training.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present invention. The following embodiments further illustrate various aspects of the present invention, but are not meant to limit the scope of the present invention.

Figure 1:
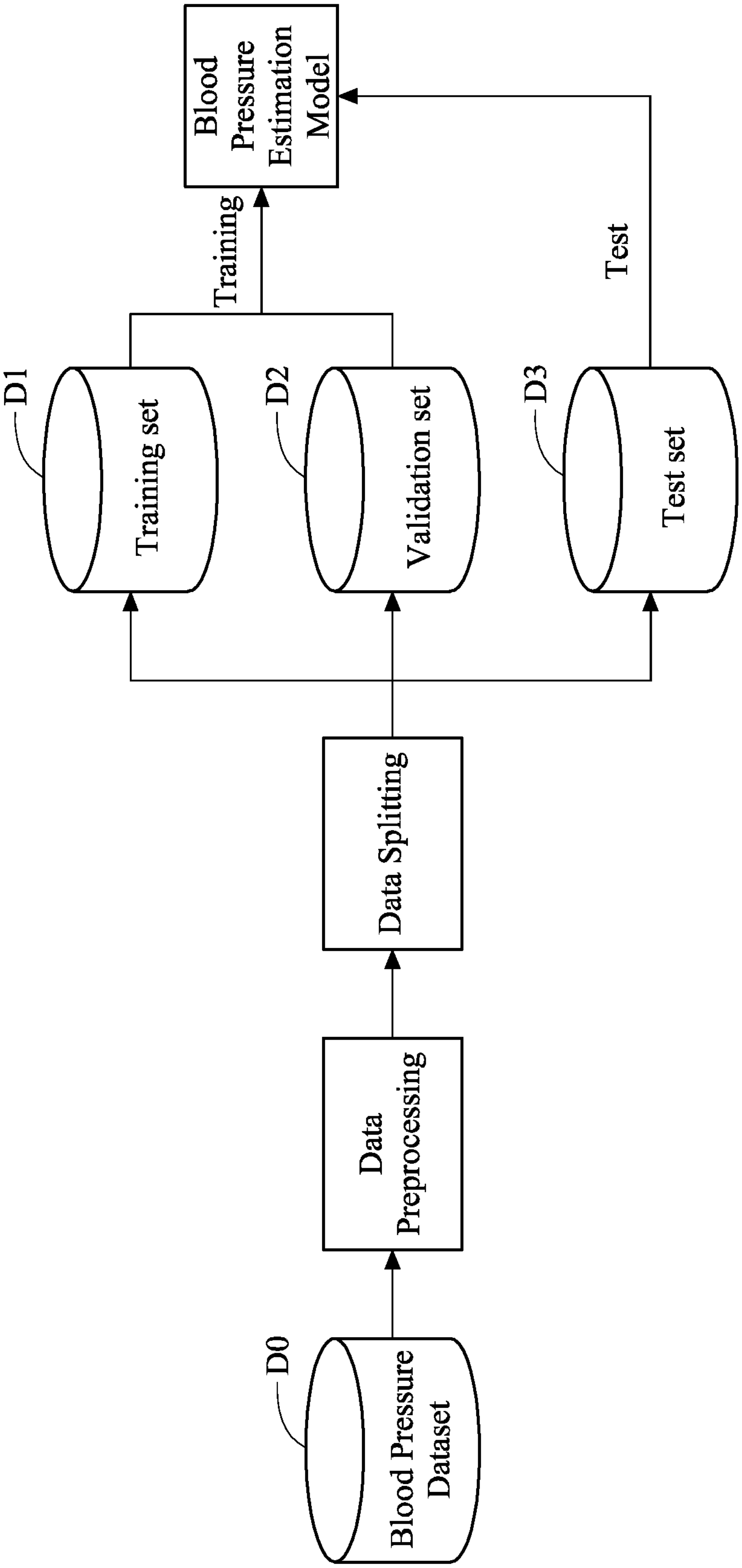
FIG. 1 is a schematic diagram of the present disclosure applied in machine learning.

FIG. 1 is a schematic diagram of the present disclosure applied in machine learning. As shown in FIG. 1, after the BP dataset D0 is preprocessed, the data splitting system and method proposed in the present disclosure may be applied to split the BP dataset D0 into training set D1, validation set D2, and test set D3. The training set D1 and the validation set D2 are configured to train and validate the BP estimation model. The test set D3 is configured to test the BP estimation model. In some application scenarios, the BP dataset is generated by preprocessing a raw dataset, and then the BP dataset is partitioned. In other words, the execution order of the data processing is not limited in the present disclosure.

Figure 2:
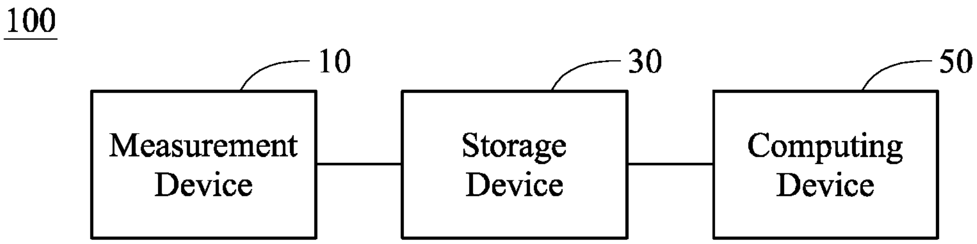
FIG. 2 is a block diagram of the data splitting system for validating machine learning according to an embodiment of the present disclosure.

FIG. 2 is a block diagram of the data splitting system for validating machine learning according to an embodiment of the present disclosure. As shown in FIG. 2, the system 100 includes a measurement device 10, a storage device 30, and a computing device 50.

The measurement device 10 is configured to generate a BP dataset, where the BP dataset includes BP data of a plurality of subjects. Each subject includes a plurality of BP data. The plurality of BP data includes a plurality of SBP data and a plurality of DBP data. In an embodiment, the measurement device 10 may be, for example, a wearable device with pulse oximetry, which applies PPG (photoplethysmography) to obtain PPG signals, and is then converted into the blood pressure data through the built-in microprocessor of the wearable device. In another embodiment, the measurement device 10 may be, for example, a wearable device with electrodes, which applies ECG (electrocardiography) technique to obtain ECG signals, and is then converted into the blood pressure data through the built-in microprocessor of the wearable device. In further another embodiment, the measurement device 10 may be, for example, an electronic sphygmomanometer or a cuff-type sphygmomanometer.

The storage device 30 is communicably connected to the measurement device for receiving and storing the BP dataset, and stores a computer-readable recording medium. In an embodiment, the storage device 30 may be volatile memory and/or non-volatile memory. The non-volatile memory includes ROM (read-only memory), PROM (programmable ROM), EPRM (electrically programmable ROM), EEPROM (electrically erasable and programmable ROM) flash memory, PRAM (phase-change random access memory), MRAM (MRAM), RRAM (resistive RAM), and/or FRAM (ferroelectric RAM). The volatile memory includes DRAM (dynamic RAM), SRAM (static RAM) and/or SDRAM (synchronous DRAM). In another embodiment, the storage device 30 may be, for example, at least one of the HDD (hard disk drive), SSD (solid-state drive), CF (compact flash) card, SD (secure digital) card, micro SD card, mini SD card, xD (extreme digital) card, and memory card.

The computing device 50 is communicably connected to the storage device 30. The computing device 50 is configured to execute the computer-readable recording medium to perform the data splitting method for validating machine learning according to an embodiment of the present disclosure. In an embodiment the computing device 50 may be, for example, a microprocessor, such as CPU (central processor unit), GPU (graphic processing unit), and/or AP (application processor); a logic chip, such as FPGA (field programmable gate array), and ASIC (application-specific integrated circuit).

Figure 3:
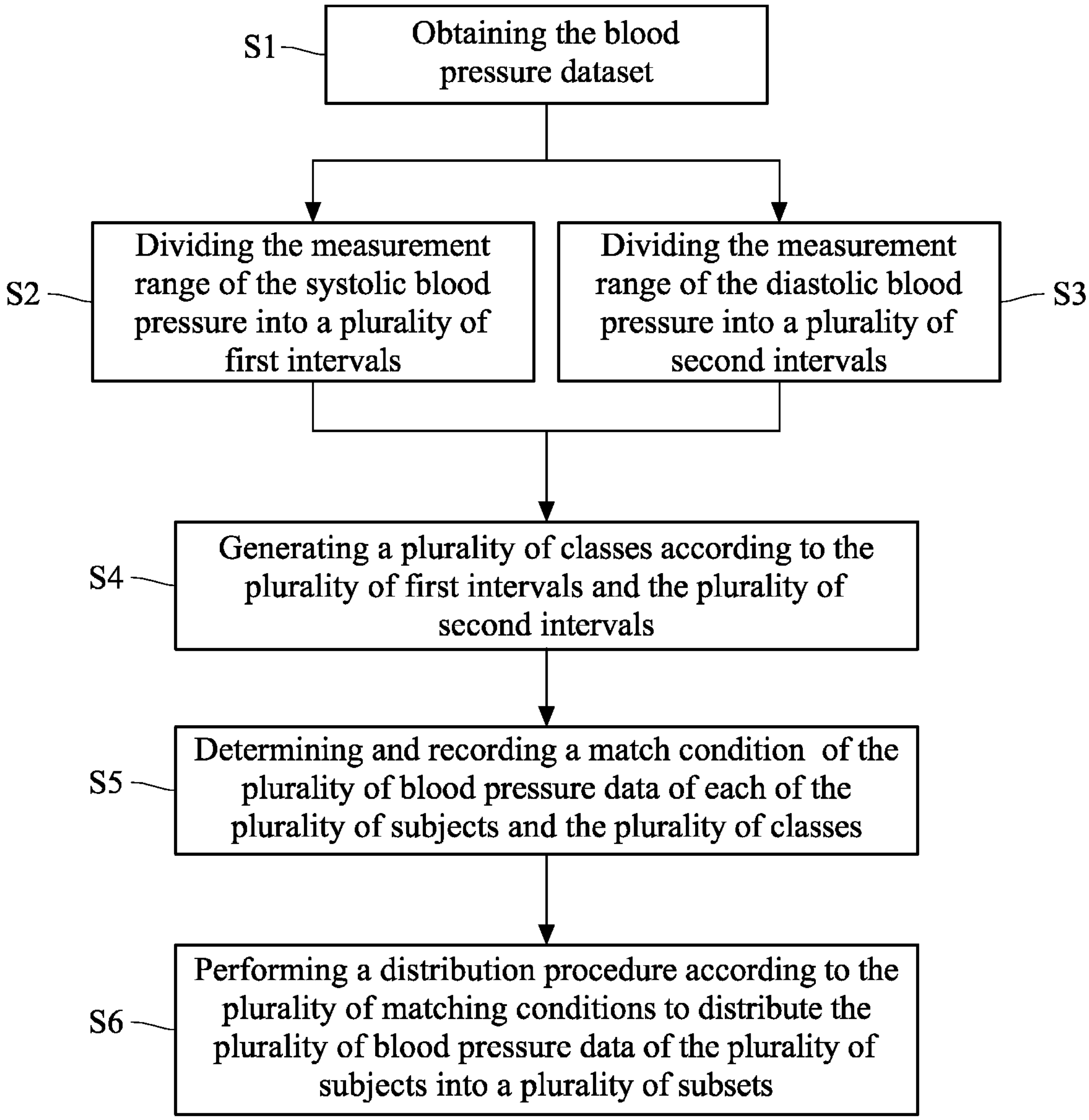
FIG. 3 is a flowchart of the data splitting method for validating machine learning according to an embodiment of the present disclosure.
Figure 4:
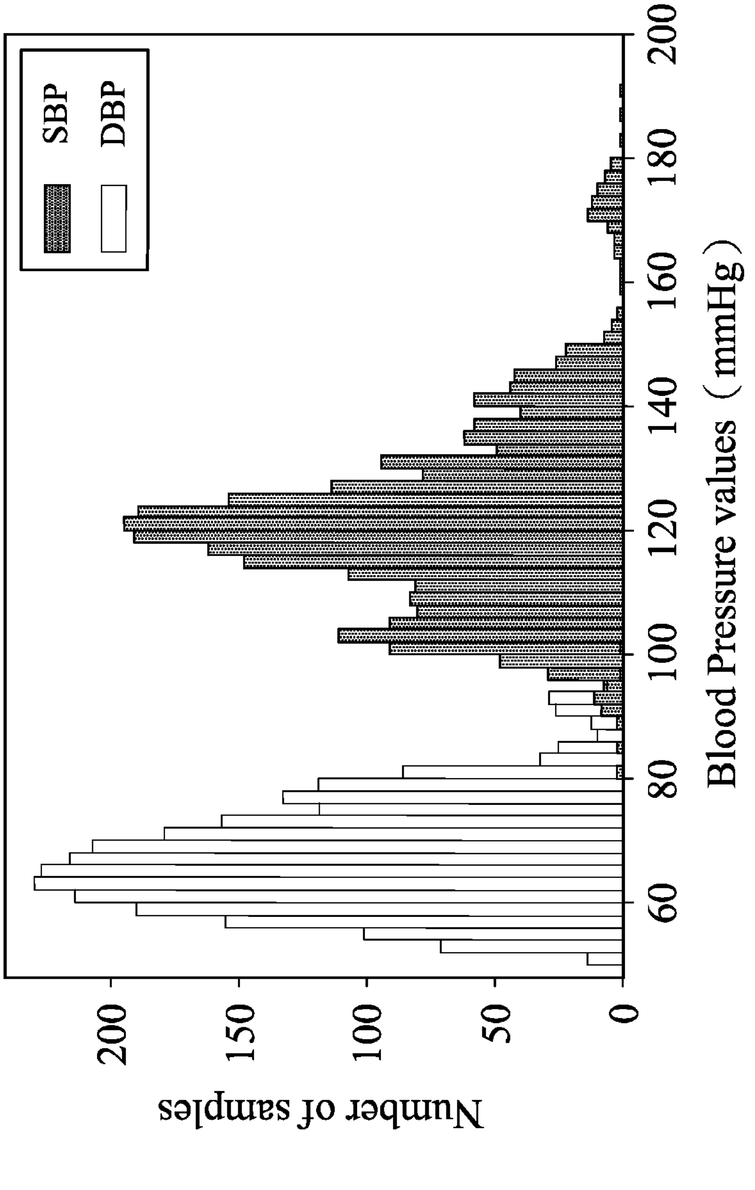
FIG. 4 is a schematic diagram of blood pressure dataset.

Please refer to FIG. 3 and FIG. 4. FIG. 3 is a flowchart of the data splitting method for validating machine learning according to an embodiment of the present disclosure, and FIG. 4 is a schematic diagram of blood pressure dataset. The method shown in FIG. 3 is suitable for a BP dataset. In an embodiment, the BP dataset includes a plurality of subjects, each subject includes a plurality of BP data, and the plurality of BP data of each subject includes a plurality of SBP data and a plurality of DBP data. However, the type of the plurality of BP data is not limited by the above two types (SBP and DBP).

The following example uses actual values to illustrate the data structure of the BP dataset. The measurement device 10 (such as an electronic sphygmomanometer) is used to measure the BP of 500 people respectively for 60 minutes. After the measurement device 10 obtains the raw measurement data of all the people, a pre-processing procedure, such as noise removal, signal sampling, may be selectively performed as required. The BP data is then extracted from the raw measurement data. Assuming that the sampling frequency is capturing 1 piece of BP data in 2 minutes, each person may contribute 30 pieces of BP data (60/2), where each piece of BP data includes a SBP value and/or a DBP value. The BP dataset described in the present disclosure may be the collection of all the BP data of the 500 people, with a total of 15,000 BP data (500*30).

The schematic diagram of the BP dataset is shown in FIG. 4. It can be seen from FIG. 4 that the distributions of both SBP and DBP are skewed. For example, there are more data records in a certain value range, such as 60-70 mmHg, while there are fewer data records in another value range, such as 150-170 mmHg.

In step S1, the computing device 50 obtains the BP dataset from the storage device 30.

In step S2, the computing device 50 divides the measurement range of SBP into a plurality of first intervals. In step S3, the computing devices divides the measurement range of DBP into a plurality of second intervals. The present disclosure does not limit the execution order of step S2 and step S3.

The following embodiment uses actual values to illustrate the divisions of first intervals and second intervals. For example, the SBP may be partitioned into four first intervals: (1) below 100 mmHg, (2) between 100 mmHg and 140 mmHg, (3) between 140 mmHg and 160 mmHg, and (4) over 160 mmHg.

The DBP may be partitioned into four second intervals: (1) below 60 mmHg, (2) between 60 mmHg and 80 mmHg, (3) between 80 mmHg and 100 mmHg, and (4) over 100 mmHg. The above values are only illustrative and not intended to limit the present disclosure. In other words, the present disclosure does not limit the size of first/second intervals, the number of the first/second intervals. In other embodiments, in addition to the above two BP constraints (SBP and DBP) shown in FIG. 3, the method of the present disclosure may further add a third BP constraint, such as pulse pressure difference, and the computing device 50 divides the measurement range of the third BP constraint into a plurality of third intervals.

In step S4, the computing device 50 generates a plurality of classes according to the plurality of first intervals and the plurality of second intervals. The quantity of classes is a product of the quantity of first intervals and the quantity of the second intervals. Referring to the above example, 16 classes (4*4) are generated according to the four first intervals and the four second intervals, as shown in Table 1 below. Each of the 16 classes includes one of the four first intervals and one of the four second intervals. For example, class 6 represents that 100≤SBP≤140 and 60≤SBP≤80.

TABLE 1

Example of classes.

| | DBP ≤ 60 | 60 ≤ DBP ≤ 80 | 80 ≤ DBP ≤ 100 | 100 ≤ DBP |
|---|---|---|---|---|
| SBP ≤ 100 | 1 | 2 | 3 | 4 |
| 100 ≤ SBP ≤ 140 | 5 | 6 | 7 | 8 |
| 140 ≤ SBP ≤ 160 | 9 | 10 | 11 | 12 |
| SBP ≤ 160 | 13 | 14 | 15 | 16 |

In step S5, the computing device 50 determines and records a match condition of the plurality of BP data of each of the plurality of subjects and the plurality of classes, and thereby generates a plurality of match conditions corresponding the plurality of subjects. Each of the plurality of match conditions includes a plurality of labels corresponding to the plurality of classes, each of the plurality of labels has one of a first state and a second state. The first state represents that at least one of the plurality of SBP data belongs to the first interval corresponding to the label corresponding to the class, and in the plurality of BP data of the same subject, at least one of the plurality of DBP data belongs to the second interval corresponding to the label corresponding to the class. The second state represents that all of the BP data do not match the class corresponding to the label. The following Table 2 uses actual values to illustrate multiple match conditions of multiple subjects in multiple classes.

TABLE 2

Example of match conditions.

| Subject | Class 1 | Class 2 | Class 3 |
|---|---|---|---|
| A | 1 | 0 | 1 |
| B | 0 | 0 | 1 |
| C | 0 | 1 | 0 |
| D | 0 | 0 | 1 |
| E | 0 | 1 | 1 |
| F | 1 | 1 | 0 |
| G | 1 | 0 | 1 |

The example shown in Table 2 includes match conditions of 9 subjects in 3 classes. Every row represents a match condition. The label "1" in the match condition denotes the first state, and the label "0" denotes the second state. For example, the match condition of subject A is (1, 0, 1), which means that in the plurality of BP data of subject A, at least one piece of BP data matches class 1, no BP data matches class 2, and at least one piece of BP data matches class 3. Overall, step S5 is configured to generate a BP class distribution of multiple subjects, the data structure of the distribution is a 0-1 matrix consisted of multiple match conditions, where the number of rows of the matrix equals the number of subjects and the number of columns of the matrix equals the number of classes.

In step S6, the computing device 50 performs a distribution procedure according to the plurality of matching conditions to distribute the plurality of blood pressure data of the plurality of subjects into a plurality of subsets. In an embodiment, one subset is equivalent to a "fold" of K-fold cross validation. The present disclosure does not limit size of a subset. The distribution procedure should consider that each class is distributed as evenly as possible into each subset, so that the SBP and DBP data distributions in different subsets may be maintained. In addition, since the distribution procedure takes the subject as the distribution unit, this method may avoid that multiple BP data from the same subject are distributed to different subsets, resulting in the breakdown of data independence.

Figure 5:
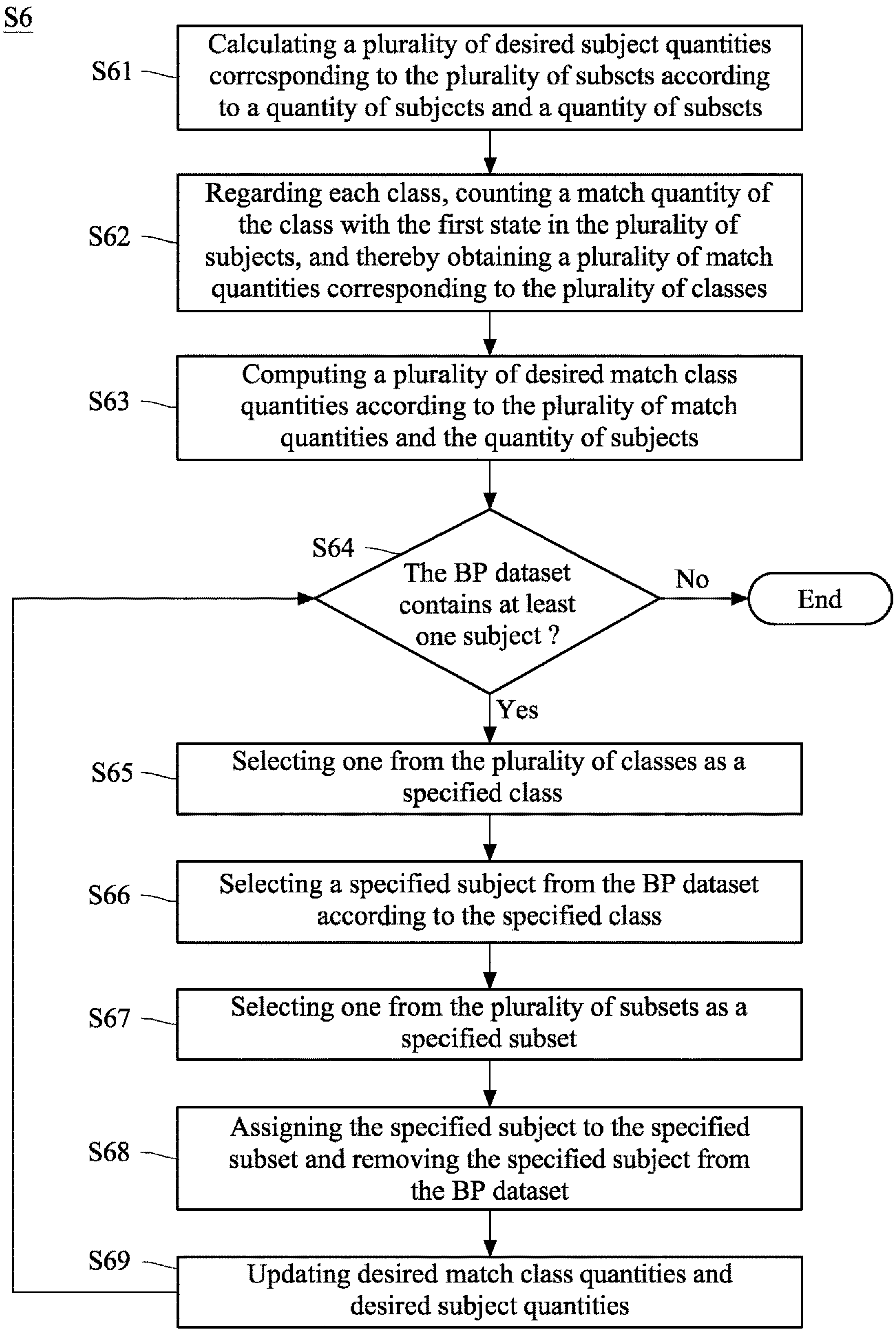
FIG. 5 is a detailed flowchart of a step in FIG. 3.

Please refer to FIG. 5. FIG. 5 is a detailed flowchart of step S6 in FIG. 3.

In step S61, the computing device 50 calculates a plurality of desired subject quantities corresponding to the plurality of subsets according to a quantity of the plurality of subjects and a quantity of the plurality of subsets. Referring to the above example and assuming that the quantity of subsets is 3, and the subsets are denoted as subset 1, subset 2, and subset 3. The quantity of subjects is 9 as the distribution example shown in Table 2. Therefore, the desired subject quantity corresponding to subset 1 is 3, the desired subject quantity corresponding to subset 2 is 3, and the desired subject quantity corresponding to subset 3 is 3. In other words, the desired subject quantity is the quantity of subjects divided by the quantity of subsets. If there is an undivisible case, the remaining unassigned subjects will be assigned to certain subsets according to the process described later.

In step S62, regarding each class, the computing device 50 counts a match quantity of this class with the first state in the plurality of subjects, and thereby obtaining a plurality of match quantities corresponding to the plurality of classes. The step S62 may be viewed as a loop procedure. The computing device 50 process one class at a time (this depends on the parallel processing ability of the computing device 50, it can also process N classes at a time), until all classes have been processed. Based on the example of match conditions shown in Table 2, the computing device 50 performs step S62 and outputs a result as Table 3 below.

TABLE 3

Example of match quantities.

| Subject | Class 1 | Class 2 | Class 3 |
|---|---|---|---|
| A | 1 | 0 | 1 |
| B | 0 | 0 | 1 |
| C | 0 | 1 | 0 |
| D | 0 | 0 | 1 |
| E | 0 | 1 | 1 |
| F | 1 | 1 | 0 |
| G | 1 | 0 | 1 |
| Match Quantity | 4 | 3 | 7 |

In step S63, the computing device 50 computes a plurality of desired match class quantities according to the plurality of match quantities and the quantity of the plurality of subsets. In an embodiment, the desired match class quantity is the average value of the match quantity divided by the quantity of subsets. Based on the example of match quantity shown in Table 3, the computing device 50 performs step S63 and outputs a result as Table 4 below. For example, the match quantity corresponding to subset 1 is 4, therefore, the desired match class quantity of every subset is 1.3 (a rounding result of 4/3).

TABLE 4

Example of the desired match class quantities and subsets

| | Subject | Class 1 | Class 2 | Class 3 |
|---|---|---|---|---|
| Subset 1 | Desired match class quantity | 1.3 | 1 | 2.3 |
| Subset 2 | Desired match class quantity | 1.3 | 1 | 2.3 |
| Subset 3 | Desired match class quantity | 1.3 | 1 | 2.3 |

In step S64, the computing device 50 determines whether there are subjects with the BP dataset that have not been assigned to the subset. If the determination is positive, the process of steps S65-S69 is executed and then the process returns to step S64 to perform a new determination. The process of steps S65-S69 is repeated until all the subjects are assigned to a certain subset. After that, the determination of step S64 becomes negative, and the data splitting method according to an embodiment of the present disclosure is finished.

In step S65, the computing device 50 selects one from the plurality of classes as a specified class. In an embodiment, the matching quantity of the specified class is minimal. For example, in Table 4, the match quantity corresponding to class 2 is minimal (2.3>1.3>1), so the computing device 50 selects class 2 as the specified class in the first iteration. In other embodiment, the computing device 50 may select the specified class randomly.

In step S66, the computing device 50 selects a specified subject from the BP dataset. The label of the specified class of the specified subject is the first state. Referring to the above example, in the first iteration, there are 9 subjects including subjects A-I in the BP dataset that have not been assigned. When the specified class is class 2, subjects C, E, F are selected as the specified subjects since the labels of the three subjects C, E, F in class 2 are all value "1", representing the first state. In addition, the process of steps S66-S69 is repeated for three times since there are three subjects being selected as specified subjects. After all specified subjects have been assigned, the computing device 50 may select a new specified subject in the next iteration.

In step S67, the computing device 50 selects one from the plurality of subsets as a specified subset. Specifically, the computing device 50 determines whether a first condition is satisfied. If the determination is positive, the specified set is generated. If the determination is negative, the computing device 50 determines whether a second condition is satisfied. If the determination is positive, the specified set is generated. If the determination is negative, the computing device 50 randomly selects one of the plurality of subsets that meet a third condition as the specified subset.

The first condition is to find a first maximum among all the desired match class quantities covered by the specified class, and the number of the first maximum is equal to 1. If the first condition is satisfied, the subset corresponding to the first maximum is the specified set.

The second condition is to find a first maximum among all the desired match class quantities covered by the specified class, and the number of the first maximum is greater than 1; and find a second maximum among all the desired subject quantities, and the number of the second maximum is equal to 1. If the second condition is satisfied, the subset corresponding to the second maximum is the specified subset.

The third condition is to find a first maximum among all the desired match class quantities covered by the specified class, and the number of the first maximum is greater than 1; and find a second maximum among all the desired subject quantities, and the number of the second maximum is greater than 1.

The following uses Table 4 as an example to illustrate the process of step S67, where the specified class is class 2 generated in step S66. The desired match class quantities covered by class 2 are (1, 1, 1) respectively. The maximum is "1" and the number of this maximum is 3, so the first condition is not satisfied. The desired subject quantities of subsets 1-3 are (3, 3, 3) respectively. The maximum is "3" and the number of maximum is 3, so the second condition is not satisfied. The subsets meeting the third condition include subset 1, subset 2, and subset 3, so the computing device 50 randomly selects one from the three subsets as the specified subset.

In step S68, the computing device 50 assigns the specified subject to the specified subset and removes the specified subject from the BP dataset. Referring to the above example, the specified subjects generated in step S66 include subjects C, E, F, and the specified subset generated in step S67 include subsets 1, 2, 3. In an embodiment, when there are multiple specified subjects generated in step S66, the computing device 50 may randomly select one subject in step S68. For example, in step S68, the computing device 50 assigns the subject C to the subset 1 and removes BP data of subject C from the BP dataset.

In step S69, the computing device 50 updates the plurality of desired match class quantities and the plurality of desired subject quantities. Referring to the above example, the result after the update is shown as Table 5 below. The desired match class quantity of class 2 in subset 1 is reduced from 1 to 0 (1−1), because the subject C has been assigned to subset 1 and the value of class 2 of subject C is "1". In addition, the desired subject quantities of subset 1 is also reduced from 3 to 2 (3−1), because the subject C has been assigned to subset 1.

TABLE 5

Example of distribution result in the first iteration.

| | Subject | Class 1 | Class 2 | Class 3 |
|---|---|---|---|---|
| Subset 1 | C | 0 | 1 | 0 |
| | Desired match class quantity | 1.3 | 0 | 2.3 |
| Subset 2 | Desired match class quantity | 1.3 | 1 | 2.3 |
| Subset 3 | Desired match class quantity | 1.3 | 1 | 2.3 |

After step S69 is finished, the process returns to step S64. Since there are subjects A-B and D-I in the BP dataset, the determination of step S64 is positive, and the second iteration of steps S65-69 is performed then.

In step S65, the desired match class quantity corresponding to class 2 is still minimal (Note that the desired match class quantity below 1 is not considered), so the computing device 50 still selects class 2 as the specified class in the second iteration.

In step S66, the specified subject selected by the computing device 50 includes subjects E, F.

In step S67, the desired match class quantities of subset 2 and subset 3 in class 2 are (1, 1) respectively. The maximum is 1 and the number of this maximum is 2, so the first condition is not satisfied. The desire subject quantities of subsets 1-3 are (2, 3, 3) respectively. The maximum is 3 and the number of this maximum is 2, so the second condition is not satisfied. The subsets meeting the third condition include subset 2 and subset 3, so the computing device 50 randomly selects one from these two subsets as the specified subset.

In step S68, for example, the specified subject E is assigned to the specified subset 2, and the specified subject E is removed from the BP dataset.

In step S69, the result after update is shown as Table 6 below. Note that the desired match class quantity of subset 2 may be decremented according to the match condition of subject E (0, 1, 1).

TABLE 6

Example of distribution result in the second iteration.

| | Subject | Class 1 | Class 2 | Class 3 |
|---|---|---|---|---|
| Subset 1 | C | 0 | 1 | 0 |
| | Desired match class quantity | 1.3 | 0 | 2.3 |
| Subset 2 | E | 0 | 1 | 1 |
| | Desired match class quantity | 1.3 | 0 | 1.3 |
| Subset 3 | Desired match class quantity | 1.3 | 1 | 2.3 |

Based on the above process, a specified subject may be assigned to a specified set every time the iteration process of steps S65-S69 is performed. Therefore, the total number of iterations is equal to the number of subjects in the BP dataset. The following tables 7, 8, 9 show the examples of the third, sixth, and last (ninth) iteration, respectively. For better understanding, this example assumes that "random selection" is implemented in alphabetical order and Arabic number order.

TABLE 7

Example of distribution result in the third iteration.

| | Subject | Class 1 | Class 2 | Class 3 |
|---|---|---|---|---|
| Subset 1 | C | 0 | 1 | 0 |
| | Desired match class quantity | 1.3 | 0 | 2.3 |
| Subset 2 | E | 0 | 1 | 1 |
| | Desired match class quantity | 1.3 | 0 | 1.3 |
| Subset 3 | F | 1 | 1 | 0 |
| | Desired match class quantity | 0.3 | 0 | 2.3 |

TABLE 8

Example of distribution result in the sixth iteration.

| | Subject | Class 1 | Class 2 | Class 3 |
|---|---|---|---|---|
| Subset 1 | C | 0 | 1 | 0 |
| | A | 1 | 0 | 1 |
| | Desired match class quantity | 0.3 | 0 | 1.3 |
| Subset 2 | E | 0 | 1 | 1 |
| | G | 1 | 0 | 1 |
| | Desired match class quantity | 0.3 | 0 | 0.3 |
| Subset 3 | F | 1 | 1 | 0 |
| | H | 1 | 0 | 1 |
| | Desired match class quantity | −0.7 | 0 | 1.3 |

TABLE 9

Example of distribution result in the ninth iteration.

| | Subject | Class 1 | Class 2 | Class 3 |
|---|---|---|---|---|
| Subset 1 | C | 0 | 1 | 0 |
| | A | 1 | 0 | 1 |
| | B | 0 | 0 | 1 |
| | Desired match class quantity | 0.3 | 0 | 0.3 |
| Subset 2 | E | 0 | 1 | 1 |
| | G | 1 | 0 | 1 |
| | I | 0 | 0 | 1 |
| | Desired match class quantity | 0.3 | 0 | −0.7 |
| Subset 3 | F | 1 | 1 | 0 |
| | H | 1 | 0 | 1 |
| | D | 0 | 0 | 1 |
| | Desired match class quantity | −0.7 | 0 | 0.3 |

Figure 6:
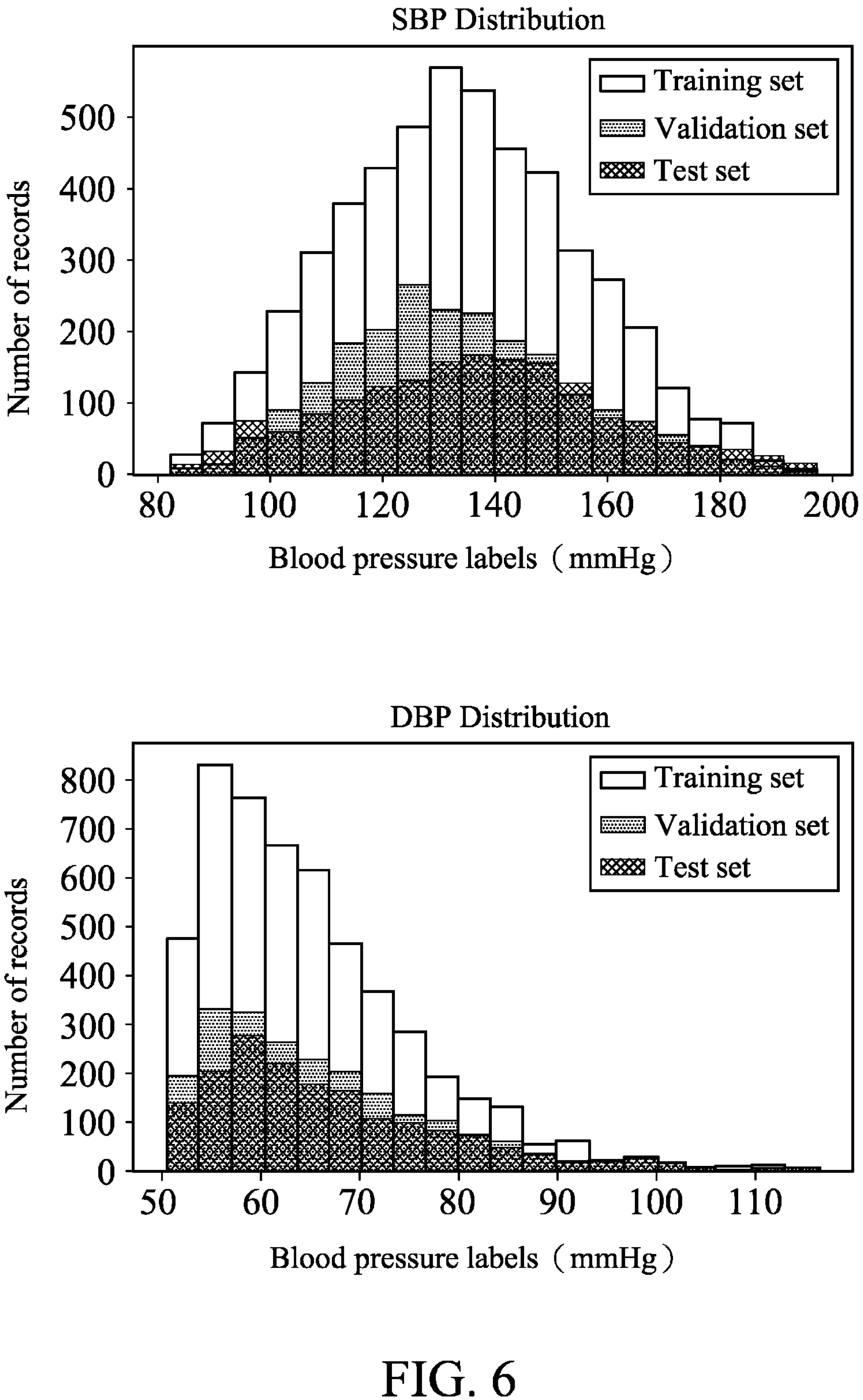
FIG. 6 is a schematic diagram of systolic blood pressure distribution and diastolic blood pressure distribution generated by a conventional data splitting method.
Figure 7:
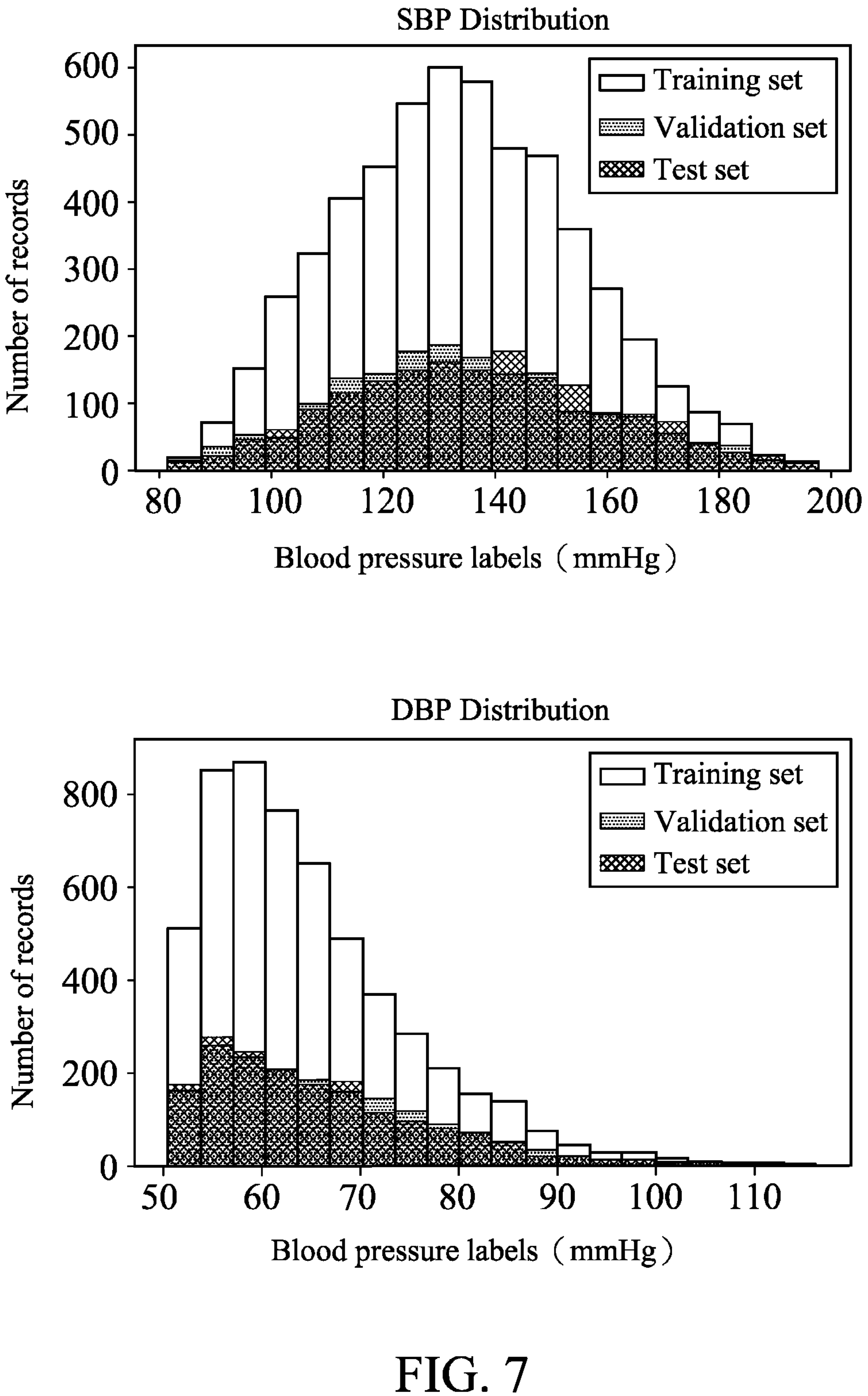
FIG. 7 is a schematic diagram of systolic blood pressure distribution and diastolic blood pressure distribution generated by the data splitting method for validating machine learning according to an embodiment of the present disclosure.

Please refer to FIG. 6 and FIG. 7. FIG. 6 is a schematic diagram of systolic blood pressure distribution and diastolic blood pressure distribution generated by a conventional data splitting method, and FIG. 7 is a schematic diagram of systolic blood pressure distribution and diastolic blood pressure distribution generated by the data splitting method for validating machine learning according to an embodiment of the present disclosure. In FIG. 6, the distributions of the training set, the validation set, and the test set are not consistent. Taking the schematic diagram of the SBP distribution in FIG. 6 as an example, the training set has the largest amount of data at about 130 mmHg, but the validation set has the largest data amount at about 125 mmHg. In addition, both the validation set and the test set contain a small amount of data at about 190 mmHg, but the training set has almost no data there. This will result in the trained BP estimation model not being able to estimate SBP above 190 mmHg. In FIG. 7, whether it is the SBP distribution or the DBP distribution, the training set, the validation set, and the test set have similar data distribution trends. For example: if a certain data set has a large amount of data in BP interval A and a small amount of data in BP interval B, other data sets may also have the same characteristics. Therefore, the proposed data splitting method helps to improve the generality and accuracy of the BP estimation model.

In view of the above, the data splitting system and method for validating machine learning proposed in the present disclosure have the following contributions or effects: (1) The proposed method keeps all samples from the same subject in the same set (either training set or test set); (2) The proposed method is able to achieve similar BP distribution in training, validation and test sets; and (3) The proposed method is able to maintain the BP distribution of different sets when there are multiple constraints, meaning SBP distribution of training/validation and test sets are similar and at the same time, DBP distribution of different sets could also be similar. Said multiple constraints include SBP and DBP, and may further include any constraints related to BP, such as pulse rate, heartbeat, that affect model training.

What is claimed is:

1. A data splitting method for validating machine learning adapted to a BP (blood pressure) dataset, wherein the BP dataset comprises a plurality of subjects, each of the plurality of subjects comprises a plurality of BP data, and the plurality of BP data of each subject includes a plurality of SBP (systolic blood pressure) data and a plurality of DBP (diastolic blood pressure) data, and the method comprises following steps performed by a computing device:

dividing a measurement range of the SBP data into a plurality of first intervals and dividing a measurement range of the DBP data into a plurality of second intervals;

generating a plurality of classes according to the plurality of first intervals and the plurality of second intervals, wherein each of the plurality of classes comprises one of the plurality of first intervals and one of the plurality of second intervals;

determining and recording a match condition of the plurality of blood pressure data of each of the plurality of subjects and the plurality of classes, and thereby generating a plurality of match conditions corresponding the plurality of subjects, wherein each of the plurality of match conditions comprises a plurality of labels corresponding to the plurality of classes, each of the plurality of labels has one of a first state and a second state, the first state represents that one of the plurality of SBP data belongs to the first interval corresponding to the label corresponding to the class and one of the plurality of DBP data belongs to the second interval corresponding to the label corresponding to the class, and the second state represents that the plurality of BP data do not match the class corresponding to the label; and performing a distribution procedure according to the plurality of matching conditions to distribute the plurality of BP data of the plurality of subjects into a plurality of subsets, wherein the distribution procedure comprises:

calculating a plurality of desired subject quantities corresponding to the plurality of subsets according to a quantity of the plurality of subjects and a quantity of the plurality of subsets;

regarding each of the plurality of classes, counting a match quantity of the class with the first state in the plurality of subjects thereby obtaining a plurality of match quantities corresponding to the plurality of classes;

computing a plurality of desired match class quantities according to the plurality of match quantities and the quantity of the plurality of subjects; and performing following steps when the BP dataset contains one or some of the plurality of subjects:

selecting one from the plurality of classes as a specified class, wherein the matching quantity of the specified class is minimal;

selecting a specified subject from the BP dataset, wherein the label of the specified class of the specified subject is the first state;

selecting one from the plurality of subsets as a specified subset according to the specified class;

assigning the specified subject to the specified subset and removing the specified subject from the BP dataset; and after the specified subject is assigned, updating the plurality of desired match class quantities and the plurality of desired subject quantities.

2. The data splitting method for validating machine learning of claim 1, wherein selecting one from the plurality of subsets as the specified subset comprises:

finding a first maximum from the plurality of desired match class quantities corresponding to the plurality of subsets; and assigning the subset corresponding to the first maximum as the specified subset when a quantity of the first maximum equals one.

3. The data splitting method for validating machine learning of claim 2, further comprising:

finding a second maximum from the plurality of desired subject quantities corresponding to the plurality of subjects when the quantity of the first maximum is greater than one; and assigning the subset corresponding to the second maximum as the specified subset when a quantity of the second maximum equals one.

4. The data splitting method for validating machine learning of claim 3, further comprising randomly selecting one from a plurality of subsets corresponding to the second maximum as the specified subset when a quantity of the second maximum is greater than one.

5. A data splitting system including at least one processor for validating machine learning comprising:

a measurement device configured executed by the at least one processor to generate a BP (blood pressure) dataset, wherein the BP dataset comprises a plurality of subjects, each of the plurality of subjects comprises a plurality of BP data and the plurality of BP data of each subject includes a plurality of SBP (systolic blood pressure) data and a plurality of DBP (diastolic blood pressure) data;

a storage device communicably connecting to the measurement device for receiving and storing the BP dataset, and configured to store a computer-readable recording medium; and a computing device communicably connecting to the storage device, wherein the computing device is configured to execute the computer-readable recording medium to perform following steps:

dividing a measurement range of the SBP data into a plurality of first intervals and dividing a measurement range of the DBP data into a plurality of second intervals;

generating a plurality of classes according to the plurality of first intervals and the plurality of second intervals, wherein each of the plurality of classes comprises one of the plurality of first intervals and one of the plurality of second intervals;

determining and recording a match condition of the plurality of blood pressure data of each of the plurality of subjects and the plurality of classes, and thereby generating a plurality of match conditions corresponding the plurality of subjects, wherein each of the plurality of match conditions comprises a plurality of labels corresponding to the plurality of classes, each of the plurality of labels has one of a first state and a second state, the first state represents that one of the plurality of SBP data belongs to the first interval corresponding to the label corresponding to the class and one of the plurality of DBP data belongs to the second interval corresponding to the label corresponding to the class, and the second state represents that the plurality of BP data do not match the class corresponding to the label;

performing a distribution procedure according to the plurality of matching conditions to distribute the plurality of BP data of the plurality of subjects into a plurality of subsets;

calculating a plurality of desired subject quantities corresponding to the plurality of subsets according to a quantity of the plurality of subjects and a quantity of the plurality of subsets;

regarding each of the plurality of classes, counting a match quantity of the class with the first state in the plurality of subjects thereby obtaining a plurality of match quantities corresponding to the plurality of classes;

computing a plurality of desired match class quantities according to the plurality of match quantities and the quantity of the plurality of subjects; and performing following steps when the BP dataset contains one or some of the plurality of subjects:

selecting one from the plurality of classes as a specified class, wherein the matching quantity of the specified class is minimal;

selecting a specified subject from the BP dataset, wherein the label of the specified class of the specified subject is the first state;

selecting one from the plurality of subsets as a specified subset according to the specified class;

assigning the specified subject to the specified subset and removing the specified subject from the BP dataset; and after the specified subject is assigned, updating the plurality of desired match class quantities and the plurality of desired subject quantities.

6. The data splitting system for validating machine learning of claim 5, wherein the computing device is further configured to perform following steps when selecting one from the plurality of subsets as the specified subset:

finding a first maximum from the plurality of desired match class quantities corresponding to the plurality of subsets; and assigning the subset corresponding to the first maximum as the specified subset when a quantity of the first maximum equals one.

7. The data splitting system for validating machine learning of claim 6, wherein the computing device is further configured to perform following steps:

finding a second maximum from the plurality of desired subject quantities corresponding to the plurality of subjects when the quantity of the first maximum is greater than one; and assigning the subset corresponding to the second maximum as the specified subset when a quantity of the second maximum equals one.

8. The data splitting system for validating machine learning of claim 7, further comprising randomly selecting one from a plurality of subsets corresponding to the second maximum as the specified subset when a quantity of the second maximum is greater than one.

* * * * *